US010863775B2

(12) United States Patent
Silvestrini (10) Patent No.: US 10,863,775 B2
(45) Date of Patent: Dec. 15, 2020

(54) CARTRIDGE ASSEMBLY COMPRISING A GUIDE SLOT (71) Applicant: Philip Morris Products S.A., Neuchatel (CH)

(72) Inventor: Patrick Charles Silvestrini, Neuchatel (CH)

(73) Assignee: Philip Morris Products S.A., Neuchatel (CH)

(*) Notice: Subject to any disclaimer, the term of this patent is extended or adjusted under 35 U.S.C. 154(b) by 314 days.

(21) Appl. No.: 16/068,990

(22) PCT Filed: Jan. 25, 2017

(86) PCT No.: PCT/EP2017/051550
§ 371 (c)(1),
(2) Date: Jul. 10, 2018

(87) PCT Pub. No.: WO2017/129617
PCT Pub. Date: Aug. 3, 2017

(65) Prior Publication Data
US 2019/0021399 A1 Jan. 24, 2019

(30) Foreign Application Priority Data
Jan. 25, 2016 (EP) .................................. 16152632

(51) Int. Cl.
A24F 47/00 (2020.01)
A61M 15/06 (2006.01)
(Continued)

(52) U.S. Cl.
CPC .......... A24F 47/008 (2013.01); A24B 15/167 (2016.11); A24D 1/14 (2013.01); A24F 7/02 (2013.01); A61M 15/06 (2013.01)

(58) Field of Classification Search
CPC .......... A24F 40/40; A24F 47/008; A24D 1/14
See application file for complete search history.

(56) References Cited

U.S. PATENT DOCUMENTS

2014/0182608 A1 7/2014 Egoyants et al.
2016/0286862 A1 10/2016 Silvetrini
2017/0095002 A1 4/2017 Silvestrini

FOREIGN PATENT DOCUMENTS

DE 10 2015 102 894 A1 8/2015
EP 2 753 201 B1 2/2016
(Continued)

OTHER PUBLICATIONS

International Search Report and Written Opinion dated Apr. 28, 2017 in PCT/EP2017/051550 filed Jan. 25, 2017.
(Continued)

Primary Examiner — Eric Yaary
(74) Attorney, Agent, or Firm — Oblon, McClelland, Maier & Neustadt, L.L.P.

(57) ABSTRACT

A cartridge assembly for an aerosol-generating system is provided, including a cartridge, housing, mouthpiece, and linkage. The cartridge includes first and second compartments each having an air inlet and outlet. The housing encloses the cartridge, and includes air inlets, air outlets, and a guide slot. The mouthpiece includes an air inlet in fluid communication with the housing air outlets. The linkage extends through the guide slot and is connected to the cartridge and the mouthpiece. The mouthpiece and the cartridge are rotatable with respect to the housing from a first position to a second position. When the cartridge is in the first position, the housing obstructs the air inlets and outlets of the first and second compartments. When the cartridge is in the second position, the air inlets and outlets of the first and second compartments are in fluid communication with the housing air inlets and outlets respectively.

16 Claims, 4 Drawing Sheets (51) Int. Cl.
      *A24B 15/167*    (2020.01)
      *A24D 1/14*      (2006.01)
      *A24F 7/02*       (2006.01)

(56) References Cited

FOREIGN PATENT DOCUMENTS

| RU | 1836039 | 8/1993 |
|----|---------|--------|
| WO | WO 2008/121610 A1 | 10/2008 |
| WO | WO 2015/000974 A1 | 1/2015 |
| WO | WO 2015/197627 A1 | 12/2015 |
| WO | WO 2017/032695 A1 | 3/2017 |
| WO | WO 2017/108983 A1 | 6/2017 |

OTHER PUBLICATIONS

Russian Notice of Allowance and Search Report dated Jun. 5, 2020 in corresponding Russian Patent Application No. 2018130677/14(049875) (with English translation), 22 pages.

CARTRIDGE ASSEMBLY COMPRISING A GUIDE SLOT

The present invention relates to a cartridge assembly for use in an aerosol-generating system and an aerosol-generating system comprising the cartridge assembly. The present invention finds particular application as a cartridge assembly comprising a nicotine source and an acid source for the generation of an aerosol comprising nicotine salt particles.

Devices for delivering nicotine to a user and comprising a nicotine source and a volatile delivery enhancing compound source are known. For example, WO 2008/121610 A1 discloses devices in which nicotine and a volatile acid, such as pyruvic acid, are reacted with one another in the gas phase to form an aerosol of nicotine salt particles that is inhaled by the user.

In WO 2008/121610 A1 the nicotine source and volatile delivery enhancing compound source may be housed in compartments that are sealed by one or more removable or frangible barriers prior to initial use of the aerosol-generating system.

However, the inclusion of one or more removable or frangible barriers may disadvantageously increase the cost and complexity of manufacturing such aerosol-generating systems. Consequently, it would be desirable to provide a cartridge assembly for use in an aerosol-generating system in which one or more volatile compounds may be retained during storage without the use of removable or frangible barriers.

According to a first aspect of the present invention there is provided a cartridge assembly for use in an aerosol-generating system, the cartridge assembly comprising a cartridge, a housing, a mouthpiece and at least one linkage. The cartridge comprises a first compartment having a first air inlet and a first air outlet, and a second compartment having a second air inlet and a second air outlet. The housing encloses the cartridge, the housing comprising an upstream housing end wall comprising a third air inlet and a fourth air inlet, and a downstream housing end wall comprising a third air outlet, a fourth air outlet, and at least one guide slot. The mouthpiece comprises an upstream mouthpiece end wall and a mouthpiece air inlet in the upstream mouthpiece end wall, the mouthpiece air inlet in fluid communication with the third air outlet and the fourth air outlet. The at least one linkage extends through the at least one guide slot and is connected to the cartridge and the upstream mouthpiece end wall. The mouthpiece and the cartridge are rotatable with respect to the housing from a first position to a second position. When the cartridge is in the first position, the upstream housing end wall obstructs the first air inlet and the second air inlet, and the downstream housing end wall obstructs the first air outlet and the second air outlet. When the cartridge is in the second position, the third air inlet is in fluid communication with the first air inlet, the third air outlet is in fluid communication with the first air outlet, the fourth air inlet is in fluid communication with the second air inlet, and the fourth air outlet is in fluid communication with the second air outlet.

As used herein with reference to the invention, the term "air inlet" is used to describe one or more apertures through which air may be drawn into a component or portion of a component of the cartridge assembly.

As used herein with reference to the invention, the term "air outlet" is used to describe one or more apertures through which air may be drawn out of a component or portion of a component of the cartridge assembly.

As used herein with reference to the invention, by "obstructed" it is meant that an air inlet or an air outlet is blocked such that airflow through the air inlet or the air outlet is substantially prevented.

Advantageously, a cartridge assembly according to the present invention may minimise or substantially prevent the loss of one or more volatile compounds stored within the cartridge assembly before the cartridge assembly is used in an aerosol-generating system. Specifically, the obstruction of the first air inlet, the first air outlet, the second air inlet and the second air outlet by the housing when the cartridge is in the first position may minimise or substantially prevent the loss of one or more volatile compounds stored within the cartridge.

Advantageously, by using a housing to obstruct the air inlets and the air outlets of the cartridge, the cartridge being rotatable with respect to the housing, a cartridge assembly according to the present invention can eliminate the need to use one or more removable or frangible barriers to seal the cartridge.

Advantageously, a cartridge assembly according to the present invention provides a reliable, consistent and simple means for activating the cartridge. Specifically, the cartridge assembly being configured so that turning the mouthpiece and the cartridge with respect to the housing to uncover the air inlets and the air outlets of the cartridge minimises the risk of user error when activating the cartridge.

The at least one guide slot may be a single guide slot and the at least one linkage may be a single linkage. Providing a single linkage and a single guide slot may simplify the manufacture and construction of the cartridge assembly.

The cartridge assembly may comprise a spindle about which the mouthpiece is rotatable with respect to the housing. Providing the cartridge assembly with a spindle about which the mouthpiece is rotatable may advantageously accommodate a guide slot and linkage that are offset from the axis of rotation of the mouthpiece. The upstream mouthpiece end wall may be substantially circular. The axis of rotation of the mouthpiece may extend through the centre of the circular upstream mouthpiece end wall.

The spindle may be secured at a downstream end to the upstream mouthpiece end wall and extend through an aperture in the downstream housing end wall, wherein the spindle is free to rotate within the aperture. The spindle may be formed integrally with the upstream mouthpiece end wall. The spindle may be formed separately from the mouthpiece and attached to the upstream mouthpiece end wall. The upstream mouthpiece end wall may comprise an aperture in which the downstream end of the spindle is received. The downstream end of the spindle may be retained within the aperture in the upstream mouthpiece end wall by an interference fit.

An upstream end of the spindle may terminate in a flange, the flange positioned on an upstream side of the downstream housing end wall.

An upstream end of the spindle may be secured to a downstream end of the cartridge. The spindle may be formed integrally with the downstream end of the cartridge. The spindle may be formed separately from cartridge and attached to the downstream end of the cartridge. The downstream end of the cartridge may comprise an aperture in which the upstream end of the spindle is received. The upstream end of the spindle may be retained within the aperture in the downstream end of the cartridge by an interference fit.

The spindle may be secured at an upstream end to the downstream housing end wall and extend through an aperture in the upstream mouthpiece end wall, wherein the spindle is free to rotate within the aperture. The spindle may be formed integrally with the downstream housing end wall. The spindle may be formed separately from the housing and attached to the downstream housing end wall. The downstream housing end wall may comprise an aperture in which the upstream end of the spindle is received. The upstream end of the spindle may be retained within the aperture in the downstream housing end wall by an interference fit.

A downstream end of the spindle may terminate in a flange, the flange positioned on a downstream side of the upstream housing end wall.

The at least one guide slot may comprise a first guide slot and a second guide slot, wherein the at least one linkage comprises a first linkage extending through the first guide slot and connected to the cartridge and the upstream mouthpiece end wall, and a second linkage extending through the second guide slot and connected to the cartridge and the upstream mouthpiece end wall. Advantageously, providing first and second guide slots and first and second linkages may eliminate the need to provide any further means for controlling the rotation of the mouthpiece with respect to the housing. For example, in embodiments in which the first guide slot and the second guide slot are provided symmetrically on opposite sides of the axis of rotation of the mouthpiece with respect to the housing, it may eliminate the need to provide a spindle extending between the mouthpiece and the housing.

The downstream housing end wall is preferably substantially circular. The at least one guide slot has preferably an arcuate shape. Preferably, the arcuate shape of the at least one guide slot has a radius of curvature extending from a centre of curvature, wherein the centre of curvature is coincident with an axis of rotation of the mouthpiece with respect to the housing. In embodiments in which the at least one guide slot comprises a first guide slot and a second guide slot, preferably each guide slot has an arcuate shape. Preferably, each guide slot has a radius of curvature extending from a centre of curvature, wherein the centre of curvature for each guide slot is coincident with an axis of rotation of the mouthpiece with respect to the housing. Preferably, the first and second arcuate guide slots extend symmetrically about the axis of rotation on opposite sides of the axis of rotation. This arrangement may be particularly advantageous in embodiments in which the cartridge assembly does not comprise a spindle or any other component connecting the mouthpiece to the housing or the cartridge, except for the first and second linkages extending through the first and second guide slots.

The at least one guide slot preferably comprises a first end and a second end, wherein, when the cartridge is in the first position, the at least one linkage is positioned at the first end of the at least one guide slot, and wherein, when the cartridge is in the second position, the at least one linkage is positioned at the second end of the at least one guide slot. In embodiments in which the at least one guide slot comprises a first guide slot and a second guide slot, preferably each guide slot has a first end and a second end, wherein, when the cartridge is in the first position, each linkage is positioned at the first end of the respective guide slot, and wherein, when the cartridge is in the second position, each linkage is positioned at the second end of the respective guide slot.

Advantageously, providing the at least one guide slot with a first end and a second end corresponding to the first position and the second position respectively may limit the range of motion of the mouthpiece and the cartridge with respect to the housing. Advantageously, limiting the range of motion may reduce or eliminate user error when activating the cartridge assembly. That is, by rotating the mouthpiece with respect to the housing until the at least one linkage reaches the second end of the at least one guide slot so that no further rotation is possible, the user knows that the mouthpiece and the cartridge have been rotated fully and correctly into the second position. Advantageously, limiting the range of motion of the mouthpiece and the cartridge with respect to the housing may prevent excessive turning of the mouthpiece and the cartridge with respect to the housing, which may damage the cartridge assembly.

The cartridge assembly may be configured so that the angular rotation of the cartridge from the first position to the second position is between about 30 degrees and about 110 degrees with respect to the housing. Configuring the cartridge assembly for an angular rotation between the first and second positions within this range may advantageously facilitate turning of the mouthpiece and the cartridge by a user from the first position to the second position in a single motion. In those embodiments in which the at least one guide slot comprises an arcuate guide slot having a first end and a second end, preferably the arc between the first end and the second end of the at least one arcuate guide slot subtends an angle of between about 30 degrees and about 110 degrees.

The cartridge and the mouthpiece may be configured for two-way rotational movement with respect to the housing so that the cartridge is rotatable from the second position to the first position. Advantageously, such a cartridge assembly provides a reliable and consistent means for deactivating the cartridge. That is, turning the cartridge and the mouthpiece into the first position from the second position re-obstructs the air inlets and the air outlets of the cartridge with the housing. This advantageously minimises or substantially prevents loss of any remaining volatile compounds stored within the cartridge when the cartridge assembly is not in use. Therefore, such a cartridge assembly may advantageously eliminate the need for a user to consume the entire volatile contents of the cartridge in a single experience, as the cartridge assembly can be deactivated after each use.

The at least one linkage may comprise a rod extending between the upstream mouthpiece end wall and the cartridge. The rod may be formed integrally with one of the upstream mouthpiece end wall and the cartridge. The rod may be formed separately from the mouthpiece and the cartridge and secured to the upstream mouthpiece end wall and the cartridge. A downstream end of the cartridge may comprise an aperture in which the upstream end of the rod is received. The upstream end of the rod may be retained within the aperture in the downstream end of the cartridge by an interference fit. The upstream mouthpiece end wall may comprise an aperture in which a downstream end of the rod is received. The downstream end of the rod may be retained within the aperture in the upstream mouthpiece end wall by an interference fit. In embodiments in which the at least one linkage comprises a first linkage and a second linkage, each linkage may comprise a rod extending between the upstream mouthpiece end wall and the cartridge, as described herein.

The mouthpiece may comprise a mouthpiece chamber positioned downstream of the upstream mouthpiece end wall and in fluid communication with the mouthpiece air inlet, and wherein the mouthpiece further comprises a mouthpiece air outlet at a downstream end of the mouthpiece chamber. Providing a mouthpiece chamber positioned downstream of the upstream mouthpiece end wall may be advantageous, in particular in embodiments in which a plurality of volatile reactants are stored separately within the cartridge. That is, the volatile reactants may be reacted in the gas phase within the mouthpiece chamber before the reaction product is delivered to a user through the mouthpiece air outlet.

The mouthpiece may comprise a ventilation air inlet providing fluid communication between the exterior of the mouthpiece and the mouthpiece chamber, wherein the ventilation air inlet is position between the upstream mouthpiece end wall and the downstream end of the mouthpiece chamber.

The cartridge assembly may comprise a nicotine source positioned within the first compartment. The cartridge assembly may comprise an acid source positioned within the second compartment.

As used herein with reference to the invention, the term "nicotine", is used to describe nicotine, nicotine base or a nicotine salt.

The nicotine source may comprise a first carrier material impregnated with between about 1 milligram and about 50 milligrams of nicotine. The nicotine source may comprise a first carrier material impregnated with between about 1 milligram and about 40 milligrams of nicotine. Preferably, the nicotine source comprises a first carrier material impregnated with between about 3 milligrams and about 30 milligrams of nicotine. More preferably, the nicotine source comprises a first carrier material impregnated with between about 6 milligrams and about 20 milligrams of nicotine. Most preferably, the nicotine source comprises a first carrier material impregnated with between about 8 milligrams and about 18 milligrams of nicotine.

In embodiments in which the first carrier material is impregnated with nicotine base or a nicotine salt, the amounts of nicotine recited herein are the amount of nicotine base or amount of ionised nicotine, respectively.

The first carrier material may be impregnated with liquid nicotine or a solution of nicotine in an aqueous or non-aqueous solvent.

The first carrier material may be impregnated with natural nicotine or synthetic nicotine. The acid source may comprise an organic acid or an inorganic acid.

Preferably, the acid source comprises an organic acid, more preferably a carboxylic acid, most preferably an alpha-keto or 2-oxo acid or lactic acid.

Advantageously, the acid source comprises an acid selected from the group consisting of 3-methyl-2-oxopentanoic acid, pyruvic acid, 2-oxopentanoic acid, 4-methyl-2-oxopentanoic acid, 3-methyl-2-oxobutanoic acid, 2-oxooctanoic acid, lactic acid and combinations thereof. Advantageously, the acid source comprises pyruvic acid or lactic acid. More advantageously, the acid source comprises lactic acid.

Advantageously, the acid source comprises a second carrier material impregnated with acid.

The first carrier material and the second carrier material may be the same or different.

Advantageously, the first carrier material and the second carrier material have a density of between about 0.1 grams/cubic centimetre and about 0.3 grams/cubic centimetre.

Advantageously, the first carrier material and the second carrier material have a porosity of between about 15 percent and about 55 percent.

The first carrier material and the second carrier material may comprise one or more of glass, cellulose, ceramic, stainless steel, aluminium, polyethylene (PE), polypropylene, polyethylene terephthalate (PET), poly(cyclohexanedimethylene terephthalate) (PCT), polybutylene terephthalate (PBT), polytetrafluoroethylene (PTFE), expanded polytetrafluoroethylene (ePTFE), and BAREX®.

The first carrier material acts as a reservoir for the nicotine.

Advantageously, the first carrier material is chemically inert with respect to nicotine.

The first carrier material may have any suitable shape and size. For example, the first carrier material may be in the form of a sheet or plug.

Advantageously, the shape and size of the first carrier material is similar to the shape and size of the first compartment of the cartridge.

The shape, size, density and porosity of the first carrier material may be chosen to allow the first carrier material to be impregnated with a desired amount of nicotine.

Advantageously, the first compartment of the cartridge may further comprise a flavourant. Suitable flavourants include, but are not limited to, menthol.

Advantageously, the first carrier material may be impregnated with between about 3 milligrams and about 12 milligrams of flavourant.

The second carrier material acts as a reservoir for the acid.

Advantageously, the second carrier material is chemically inert with respect to the acid. The second carrier material may have any suitable shape and size. For example, the second carrier material may be in the form of a sheet or plug.

Advantageously, the shape and size of the second carrier material is similar to the shape and size of the second compartment of the cartridge.

The shape, size, density and porosity of the second carrier material may be chosen to allow the second carrier material to be impregnated with a desired amount of acid.

Advantageously, acid source is a lactic acid source comprising a second carrier material impregnated with between about 2 milligrams and about 60 milligrams of lactic acid.

Preferably, the lactic acid source comprises a second carrier material impregnated with between about 5 milligrams and about 50 milligrams of lactic acid. More preferably, the lactic acid source comprises a second carrier material impregnated with between about 8 milligrams and about 40 milligrams of lactic acid. Most preferably, the lactic acid source comprises a second carrier material impregnated with between about 10 milligrams and about 30 milligrams of lactic acid.

The shape and dimensions of the first compartment of the cartridge may be chosen to allow a desired amount of nicotine to be housed in the cartridge.

The shape and dimensions of the second compartment of the cartridge may be chosen to allow a desired amount of acid to be housed in the cartridge.

The ratio of nicotine and acid required to achieve an appropriate reaction stoichiometry may be controlled and balanced through variation of the volume of the first compartment relative to the volume of the second compartment.

The first air inlet of the first compartment of the cartridge and the second air inlet of the second compartment of the cartridge may each comprise one or more apertures. For example, the first air inlet of the first compartment of the cartridge and the second air inlet of the second compartment of the cartridge may each comprise one, two, three, four, five, six or seven apertures.

The first air inlet of the first compartment of the cartridge and the second air inlet of the second compartment of the cartridge may comprise the same or different numbers of apertures.

Advantageously, the first air inlet of the first compartment of the cartridge and the second air inlet of the second compartment of the cartridge each comprise a plurality of apertures. For example, the first air inlet of the first compartment of the cartridge and the second air inlet of the second compartment of the cartridge may each comprise two, three, four, five, six or seven apertures.

Providing a first compartment having a first air inlet comprising a plurality of apertures and a second compartment having a second air inlet comprising a plurality of apertures may advantageously result in more homogeneous airflow within the first compartment and the second compartment, respectively. In use, this may improve entrainment of nicotine in an air stream drawn through the first compartment and improve entrainment of acid in an air stream drawn through the second compartment.

The ratio of nicotine and acid required to achieve an appropriate reaction stoichiometry may be controlled and balanced through variation of the volumetric airflow through the first compartment of the cartridge relative to the volumetric airflow through the second compartment of the cartridge. The ratio of the volumetric airflow through the first compartment relative to the volumetric airflow through the second compartment may be controlled through variation of one or more of the number, dimensions and location of the apertures forming the first air inlet of the first compartment of the cartridge relative to the number, dimensions and location of the apertures forming the second air inlet of the second compartment of the cartridge.

In embodiments in which the acid source comprises lactic acid, advantageously the flow area of the second air inlet of the second compartment of the cartridge is greater than the flow area of the first air inlet of the first compartment of the cartridge.

As used herein with reference to the invention, the term "flow area" is used to describe the cross-sectional area of an air inlet or air outlet through which airflows during use. In embodiments in which an air inlet or air outlet comprises a plurality of apertures, the flow area of the air inlet or air outlet is the total flow area of the air inlet or air outlet and is equal to the sum of the flow areas of each of the plurality of apertures forming the air inlet or air outlet. In embodiments in which the cross-sectional area of an air inlet or air outlet varies in the direction of airflow, the flow area of the air inlet or air outlet is the minimum cross-sectional area in the direction of airflow.

Increasing the flow area of the second air inlet of the second compartment of the cartridge relative to the flow area of the first air inlet of the first compartment of the cartridge advantageously increases the volumetric airflow through the second air inlet compared to the volumetric airflow through the first air inlet.

In embodiments in which the acid source comprises lactic acid, preferably the ratio of the flow area of the first air inlet of the first compartment of the cartridge to the flow area of the second air inlet of the second compartment of the cartridge is between about 3:4 and about 1:2. More preferably, the ratio of the flow area of the first air inlet of the first compartment of the cartridge to the flow area of the second air inlet of the second compartment of the cartridge is between about 2:3 and about 1:2.

The flow area of the second air inlet of the second compartment of the cartridge may be increased relative to the flow area of the first air inlet of the first compartment of the cartridge by one or both of increasing the size of the one or more apertures forming the second air inlet relative to the size of the one or more apertures forming the first air inlet and increasing the number of apertures forming the second air inlet relative to the number of apertures forming the first air inlet.

Advantageously, the flow area of the second air inlet of the second compartment of the cartridge is increased relative to the flow area of the first air inlet of the first compartment of the cartridge by increasing the number of apertures forming the second air inlet relative to the number of apertures forming the first air inlet.

Advantageously, the first air inlet of the first compartment of the cartridge comprises between 2 and 5 apertures.

Advantageously, the second air inlet of the second compartment of the cartridge comprises between 3 and 7 apertures.

Advantageously, the flow area of the first air inlet of the first compartment of the cartridge is between about 0.1 square millimetres and about 1.6 square millimetres, more advantageously between about 0.2 square millimetres and about 0.8 square millimetres.

In embodiments in which the first air inlet of the first compartment of the cartridge comprises a plurality of apertures, the apertures may have different flow areas so that the flow area of the first air inlet of the first compartment of the cartridge is divided unequally between the apertures forming the first air inlet.

In embodiments in which the first air inlet of the first compartment of the cartridge comprises a plurality of apertures, each of the apertures may have the same flow area so that the flow area of the first air inlet of the first compartment of the cartridge is divided equally between the apertures forming the first air inlet. Providing a first compartment having a first air inlet comprising a plurality of apertures having substantially the same flow area may advantageously simplify manufacturing of the cartridge.

The first air inlet of the first compartment of the cartridge may comprise one or more apertures having any suitable cross-sectional shape. For example, the cross-sectional shape of each aperture may be circular, elliptical, square or rectangular. Advantageously, each aperture has a substantially circular cross-sectional shape. Advantageously, the diameter of each aperture is between about 0.2 millimetres and about 0.6 millimetres.

In embodiments in which the acid source comprises lactic acid, advantageously the flow area of the second air inlet of the second compartment of the cartridge is between about 0.2 square millimetres and about 2.4 square millimetres, more advantageously between about 0.4 square millimetres and about 1.2 square millimetres.

In embodiments in which the second air inlet of the second compartment of the cartridge comprises a plurality of apertures, the apertures may have different flow areas so that the total flow area of the second air inlet of the second compartment of the cartridge is divided unequally between the apertures forming the second air inlet.

In embodiments in which the second air inlet of the second compartment of the cartridge comprises a plurality of apertures, each of the apertures may have the same flow area so that the total flow area of the second air inlet of the second compartment of the cartridge is divided equally between the apertures forming the second air inlet. Providing a second compartment having a second air inlet comprising a plurality of apertures having substantially the same flow area may advantageously simplify manufacturing of the cartridge.

The second air inlet of the second compartment of the cartridge may comprise one or more apertures having any suitable cross-sectional shape. For example, the cross-sectional shape of each aperture may be circular, elliptical, square or rectangular. Advantageously, each aperture has a substantially circular cross-sectional shape. Advantageously, the diameter of each aperture is between about 0.2 millimetres and about 0.6 millimetres.

The first air outlet of the first compartment of the cartridge and the second air outlet of the second compartment of the cartridge may each comprise one or more apertures. For example, the first air outlet of the first compartment of the cartridge and the second air outlet of the second compartment of the cartridge may each comprise one, two, three, four, five, six or seven apertures.

The first air outlet of the first compartment of the cartridge and the second air outlet of the second compartment of the cartridge may comprise the same or different numbers of apertures.

Advantageously, the first air outlet of the first compartment of the cartridge and the second air outlet of the second compartment of the cartridge may each comprise a plurality of apertures. For example, the first air outlet of the first compartment of the cartridge and the second air outlet of the second compartment of the cartridge may each comprise two, three, four, five, six or seven apertures. Providing a first compartment having a first air outlet comprising a plurality of apertures and a second compartment having a second air outlet comprising a plurality of apertures may advantageously result in more homogeneous airflow within the first compartment and the second compartment, respectively. In use, this may improve entrainment of nicotine in an air stream drawn through the first compartment and improve entrainment of acid in an air stream drawn through the second compartment.

In embodiments in which the first air outlet of the first compartment of the cartridge comprises a plurality of apertures, advantageously the first air outlet comprises between 2 and 5 apertures.

In embodiments in which the second air outlet of the second compartment of the cartridge comprises a plurality of apertures, advantageously, the second air outlet comprises between 3 and 7 apertures.

Advantageously, the first air outlet of the first compartment of the cartridge and the second air outlet of the second compartment of the cartridge may each comprise a single aperture. Providing a first compartment having a first air outlet comprising a single aperture and a second compartment having a second air outlet comprising a single aperture may advantageously simplify manufacturing of the cartridge.

The ratio of nicotine and acid required to achieve an appropriate reaction stoichiometry may be controlled and balanced through variation of the volumetric airflow through the first compartment of the cartridge relative to the volumetric airflow through the second compartment of the cartridge. The ratio of the volumetric airflow through the first compartment relative to the volumetric airflow through the second compartment may be controlled through variation of one or more of the number, dimensions and location of the apertures forming the first air outlet of the first compartment of the cartridge relative to the number, dimensions and location of the apertures forming the second air outlet of the second compartment of the cartridge.

The flow area of the first air outlet of the first compartment may be the same as or different to the flow area of the second air outlet of the second compartment.

The flow area of the second air outlet of the second compartment of the cartridge may be greater than flow area of the first air outlet of the first compartment of the cartridge.

Increasing the flow area of the second air outlet of the second compartment of the cartridge relative to the flow area of the first air outlet of the first compartment of the cartridge may advantageously increase the volumetric airflow through the second air outlet compared to the volumetric airflow through the first air outlet.

In embodiments in which the acid source comprises lactic acid, the ratio of the flow area of the first air outlet of the first compartment of the cartridge to the flow area of the second air outlet of the second compartment of the cartridge is preferably between about 3:4 and about 1:2. More preferably, the ratio of the flow area of the first air outlet of the first compartment of the cartridge to the flow area of the second air outlet of the second compartment of the cartridge is between about 2:3 and about 1:2.

In embodiments in which the flow area of the second air outlet of the second compartment of the cartridge is greater than flow area of the first air outlet of the first compartment of the cartridge, the flow area of the second air outlet of the second compartment of the cartridge may be increased relative to the flow area of the first air outlet of the first compartment of the cartridge by one or both of increasing the size of the one or more apertures forming the second air outlet relative to the size of the one or more apertures forming the first air outlet and increasing the number of apertures forming the second air outlet relative to the number of apertures forming the first air outlet.

Advantageously, the flow area of the second air outlet of the second compartment of the cartridge is increased relative to the flow area of the first air outlet of the first compartment of the cartridge by increasing the number of apertures forming the second air outlet relative to the number of apertures forming the first air outlet.

The first air inlet and the first air outlet of the first compartment of the cartridge may comprise the same or different numbers of apertures.

Advantageously, the first air inlet and the first air outlet of the first compartment of the cartridge comprise the same numbers of apertures. Providing a first compartment having a first air inlet and a first air outlet comprising the same number of apertures may advantageously simplify manufacturing of the cartridge.

The second air inlet and the second air outlet of the second compartment of the cartridge may comprise the same or different numbers of apertures.

Advantageously, the second air inlet and the second air outlet of the second compartment of the cartridge comprise the same numbers of apertures. Providing a second compartment having a second air inlet and a second air outlet comprising the same number of apertures may advantageously simplify manufacturing of the cartridge.

Advantageously, the flow area of the first air outlet of the first compartment of the cartridge is between about 0.1 square millimetres and about 5 square millimetres.

In embodiments in which the first air outlet of the first compartment of the cartridge comprises a plurality of apertures, the apertures may have different flow areas so that the flow area of the first air outlet of the first compartment of the cartridge is divided unequally between the apertures forming the first air outlet.

In embodiments in which the first air outlet of the first compartment of the cartridge comprises a plurality of apertures, each of the apertures may have the same flow area so that the flow area of the first air outlet of the first compartment of the cartridge is divided equally between the apertures forming the first air outlet. Providing a first compartment having a first air outlet comprising a plurality of apertures having substantially the same flow area may advantageously simplify manufacturing of the cartridge.

The first air outlet of the first compartment of the cartridge may comprise one or more apertures having any suitable cross-sectional shape. For example, the cross-sectional shape of each aperture may be circular, elliptical, square or rectangular. In embodiments in which the first air outlet of the first compartment of the cartridge comprises a plurality of apertures, advantageously each aperture has a substantially circular cross-sectional shape. In such embodiments, advantageously the diameter of each aperture is between about 0.2 millimetres and about 0.6 millimetres.

The dimensions of the one or more apertures forming the first air inlet of the first compartment of the cartridge may be the same as or different to the dimensions of the one or more apertures forming the first air outlet of the first compartment of the cartridge.

Advantageously, the dimensions of the one or more apertures forming the first air inlet of the first compartment of the cartridge may be substantially the same as the dimensions of the one or more apertures forming the first air outlet of the first compartment of the cartridge. Providing a first compartment having a first air inlet and a first air outlet comprising one or more apertures of substantially the same dimensions may advantageously simplify manufacturing of the cartridge.

Advantageously, the dimensions of the one or more apertures forming the first air outlet of the first compartment of the cartridge may be greater than the dimensions of the one or more apertures forming the first air inlet of the first compartment of the cartridge. Increasing the dimensions of the apertures forming the first air outlet of the first compartment of the cartridge relative to the dimensions of the apertures forming the first air inlet of the first compartment of the cartridge may advantageously reduce the risk of the first air outlet of the first compartment of the cartridge becoming obstructed by, for example, dust.

Advantageously, the flow area of the second air outlet of the second compartment of the cartridge is between about 0.1 square millimetres and about 5 square millimetres. In embodiments in which the second air outlet of the second compartment of the cartridge comprises a plurality of apertures, the apertures may have different flow areas so that the total flow area of the second air outlet of the second compartment of the cartridge is divided unequally between the apertures forming the second air outlet.

In embodiments in which the second air outlet of the second compartment of the cartridge comprises a plurality of apertures, each of the apertures may have the same flow area so that the total flow area of the second air outlet of the second compartment of the cartridge is divided equally between the apertures forming the second air outlet. Providing a second compartment having a second air outlet comprising a plurality of apertures having substantially the same flow area may advantageously simplify manufacturing of the cartridge.

The second air outlet of the second compartment of the cartridge may comprise one or more apertures having any suitable cross-sectional shape. For example, the cross-sectional shape of each aperture may be circular, elliptical, square or rectangular. In embodiments in which the second air outlet of the second compartment of the cartridge comprises a plurality of apertures, advantageously each aperture has a substantially circular cross-sectional shape. In such embodiments, advantageously the diameter of each aperture is between about 0.2 millimetres and about 0.6 millimetres.

The dimensions of the one or more apertures forming the second air inlet of the second compartment of the cartridge may be the same as or different to the dimensions of the one or more apertures forming the second air outlet of the second compartment of the cartridge.

Advantageously, the dimensions of the one or more apertures forming the second air inlet of the second compartment of the cartridge may be substantially the same as the dimensions of the one or more apertures forming the second air outlet of the second compartment of the cartridge. Providing a second compartment having a second air inlet and a second air outlet comprising one or more apertures of substantially the same dimensions may advantageously simplify manufacturing of the cartridge.

Advantageously, the dimensions of the one or more apertures forming the second air outlet of the second compartment of the cartridge may be greater than the dimensions of the one or more apertures forming the second air inlet of the second compartment of the cartridge. Increasing the dimensions of the apertures forming the second air outlet of the second compartment of the cartridge relative to the dimensions of the apertures forming the second air inlet of the second compartment of the cartridge may advantageously reduce the risk of the second air outlet of the second compartment of the cartridge becoming obstructed by, for example, dust.

In embodiments in which the cartridge assembly comprises a nicotine source positioned within the first compartment and an acid source positioned within the second compartment, nicotine vapour released from the nicotine source in the first compartment of the cartridge and acid vapour released from the acid source in the second compartment of the cartridge may react with one another in the gas phase in the mouthpiece to form an aerosol of nicotine salt particles.

The cartridge assembly may comprise one or more aerosol-modifying agents positioned within the mouthpiece. For example, mouthpiece may contain one or more sorbents, one or more flavourants, one or more chemesthetic agents or a combination thereof.

The first compartment and the second compartment may be arranged symmetrically with respect to each other within the cartridge.

Advantageously, the cartridge is an elongate cartridge. In embodiments in which the cartridge is an elongate cartridge, the first compartment and the second compartment of the cartridge may be arranged symmetrically about the longitudinal axis of the cartridge.

The cartridge may have any suitable transverse cross-sectional shape. For example, the transverse cross-sectional shape of the cartridge may be circular, semi-circular, elliptical, triangular, square, rectangular or trapezoidal.

The cartridge may have any suitable size.

For example, the cartridge may have a length of between about 5 millimetres and about 50 millimetres. Advantageously, the cartridge may have a length between about 10 millimetres and about 20 millimetres.

For example, the cartridge may have a width of between about 4 millimetres and about 10 millimetres and a height of between about 4 millimetres and about 10 millimetres. Advantageously, the cartridge may have a width of between about 6 millimetres and about 8 millimetres and a height of between about 6 millimetres and about 8 millimetres.

The cartridge, the housing, the mouthpiece and the at least one linkage may be formed from any suitable material or combination of materials. Suitable materials include, but are not limited to, aluminium, polyether ether ketone (PEEK), polyimides, such as Kapton®, polyethylene terephthalate (PET), polyethylene (PE), high-density polyethylene (HDPE), polypropylene (PP), polystyrene (PS), fluorinated ethylene propylene (FEP), polytetrafluoroethylene (PTFE), polyoxymethylene (POM), epoxy resins, polyurethane resins, vinyl resins, liquid crystal polymers (LCP) and modified LCPs, such as LCPs with graphite or glass fibres.

The cartridge, the housing, the mouthpiece and the at least one linkage may be formed from the same or different materials.

The cartridge may be formed from one or more materials that are nicotine-resistant and acid-resistant.

The first compartment of the cartridge may be coated with one or more nicotine-resistant materials and the second compartment of the cartridge may be coated with one or more acid-resistant materials.

Examples of suitable nicotine-resistant materials and acid-resistant materials include, but are not limited to, polyethylene (PE), polypropylene (PP), polystyrene (PS), fluorinated ethylene propylene (FEP), polytetrafluoroethylene (PTFE), epoxy resins, polyurethane resins, vinyl resins and combinations thereof.

Use of one or more nicotine-resistant materials to one or both of form the cartridge and coat the interior of the first compartment of the cartridge may advantageously enhance the shelf life of the cartridge.

Use of one or more acid-resistant materials to one or both of form the cartridge and coat the interior of the second compartment of the cartridge may advantageously enhance the shelf life of the cartridge.

The cartridge assembly may comprise a heater configured to heat the first compartment and the second compartment. In such embodiments, the heater is advantageously located between the first compartment and the second compartment. That is the first compartment and the second compartment are disposed on either side of the heater.

The heater may be an electrical heater. The heater may be a resistive heater.

Advantageously, the heater is configured to heat the first compartment and the second compartment of the cartridge to a temperature of below about 250 degrees Celsius. Preferably, the heater is configured to heat the first compartment and the second compartment of the cartridge to a temperature of between about 80 degrees Celsius and about 150 degrees Celsius.

Advantageously, the heater is configured to heat the first compartment and the second compartment of the cartridge to substantially the same temperature.

As used herein with reference to the invention, by "substantially the same temperature" it is meant that the difference in temperature between the first compartment and the second compartment of the cartridge measured at corresponding locations relative to the heater is less than about 3° C.

The cartridge may comprise a third compartment for receiving a heating element of an aerosol-generating device. Preferably, the third compartment is positioned between the first compartment and the second compartment. That is, the first compartment and the second compartment are disposed on either side of the third compartment. Preferably, the upstream housing end wall comprises an aperture aligned with the third compartment when the cartridge is in the second position. In use, a heating element of an aerosol-generating device is received within the third compartment to heat the first compartment and the second compartment.

The cartridge may comprise a susceptor for inductively heating the first compartment and the second compartment. In such embodiments, the susceptor is advantageously located between the first compartment and the second compartment. That is, the first compartment and the second compartment are disposed on either side of the susceptor.

In use, heating the first compartment and the second compartment of the cartridge to a temperature above ambient temperature advantageously enables control of the vapour concentrations of volatile compounds stored within the first and second compartments. For example, in embodiments in which the cartridge assembly comprises a nicotine source positioned within the first compartment and an acid source positioned within the second compartment, heating the first and second compartments enables the vapour pressure of nicotine in the first compartment and the vapour pressure of acid in the second compartment to be controlled and balanced proportionally to yield an efficient reaction stoichiometry between the nicotine and the acid. Advantageously, this may improve the efficiency of the formation of nicotine salt particles and the consistency of delivery to a user. Advantageously, it may also reduce the delivery of unreacted nicotine and unreacted acid to a user.

The cartridge may be formed from one or more thermally conductive materials.

The first compartment of the cartridge and the second compartment of the cartridge may be coated with one or more thermally conductive materials.

Use of one or more thermally conductive materials to one or both of form the cartridge and coat the interior of the first compartment and the second compartment of the cartridge may advantageously increase heat transfer from a heater or a susceptor to the nicotine source and the acid source.

Suitable thermally conductive materials include, but are not limited to, metals such as, for example, aluminium, chromium, copper, gold, iron, nickel and silver, alloys, such as brass and steel and combinations thereof.

The cartridge may be formed of one or more materials having a low resistivity or a high resistivity depending on whether the first compartment and the second compartment are heated by conduction or induction.

The first compartment of the cartridge and the second compartment of the cartridge may be coated with one or more materials having a low resistivity or a high resistivity depending on whether the first compartment and the second compartment are heated by conduction or induction.

The cartridge may be formed by any suitable method. Suitable methods include, but are not limited to, deep drawing, injection moulding, blistering, blow forming and extrusion.

The cartridge assembly may be designed to be disposed of once the nicotine in the first compartment and the acid in the second compartment are depleted.

The cartridge may be designed to be refillable.

The cartridge assembly may simulate the shape and dimensions of a combustible smoking article, such as a cigarette, a cigar, or a cigarillo. Advantageously, in such embodiments the cartridge assembly may simulate the shape and dimensions of a cigarette.

The cartridge assembly may be configured for engagement with the housing of an aerosol-generating device. Preferably, at least one of the housing and the mouthpiece is configured for engagement with the housing of an aerosol-generating device.

According to a second aspect of the present invention there is provided an aerosol-generating system comprising an aerosol-generating device and a cartridge assembly according to the first aspect of the present invention, in accordance with any of the embodiments described herein.

The aerosol-generating device comprises a device cavity configured to receive an upstream end of the cartridge assembly and a heater for heating the first compartment and the second compartment of the cartridge.

In those embodiments in which the cartridge comprises a third compartment for receiving a heating element, the heater of the aerosol-generating device advantageously comprises a heating element positioned within the device cavity and configured to be received within the third compartment of the cartridge when the upstream end of the cartridge assembly is received within the device cavity. The heating element may be a resistive heating element. In use, the heating element is received within the third compartment and heats the first compartment and the second compartment.

In those embodiments in which the cartridge comprises a susceptor positioned between the first compartment and the second compartment, the heater of the aerosol-generating device advantageously comprises an inductive heater surrounding at least a portion of the device cavity. In use, the inductive heater inductively heats the susceptor, which heats the first compartment and the second compartment.

Advantageously, the heater of the aerosol-generating device is configured to heat the first compartment and the second compartment of the cartridge to a temperature of below about 250 degrees Celsius. Preferably, the heater of the aerosol-generating device is configured to heat the first compartment and the second compartment of the cartridge to a temperature of between about 80 degrees Celsius and about 150 degrees Celsius.

Advantageously, the heater of the aerosol-generating device is configured to heat the first compartment and the second compartment of the cartridge to substantially the same temperature.

The aerosol-generating device may further comprise a power supply for supplying power to the heater and a controller configured to control a supply of power from the power supply to the heater.

The aerosol-generating device may comprise one or more temperature sensors configured to sense the temperature of at least one of the heater, the first compartment, and the second compartment. In such embodiments, the controller may be configured to control a supply of power to the heater based on a sensed temperature.

For the avoidance of doubt, features described above in relation to one aspect of the invention may also be applicable to other aspects of the invention. In particular, features described above in relation to the cartridge assembly of the invention may also relate, where appropriate, to the aerosol-generating systems of the invention, and vice versa.

Embodiments of the invention will now be described, by way of example only, with reference to the accompanying drawings, in which.

Figure 1:
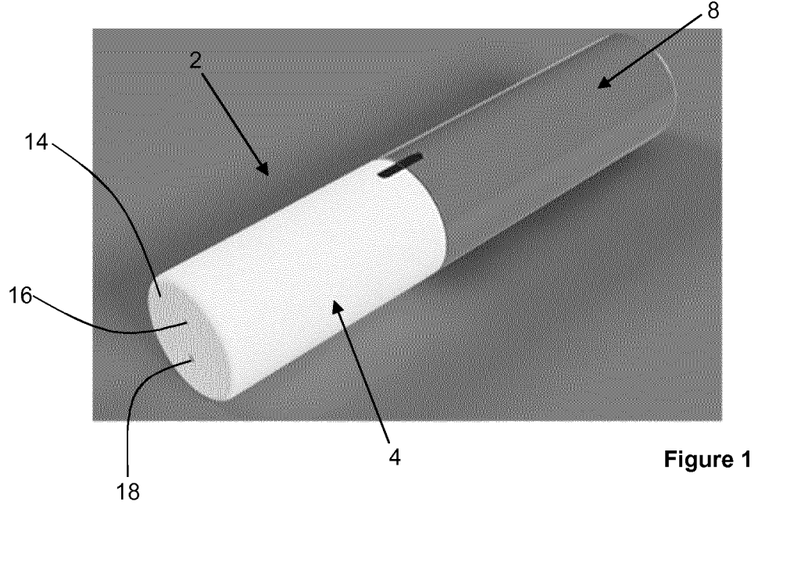
FIG. 1 shows a cartridge assembly in accordance with an embodiment of the present invention.
Figure 2:
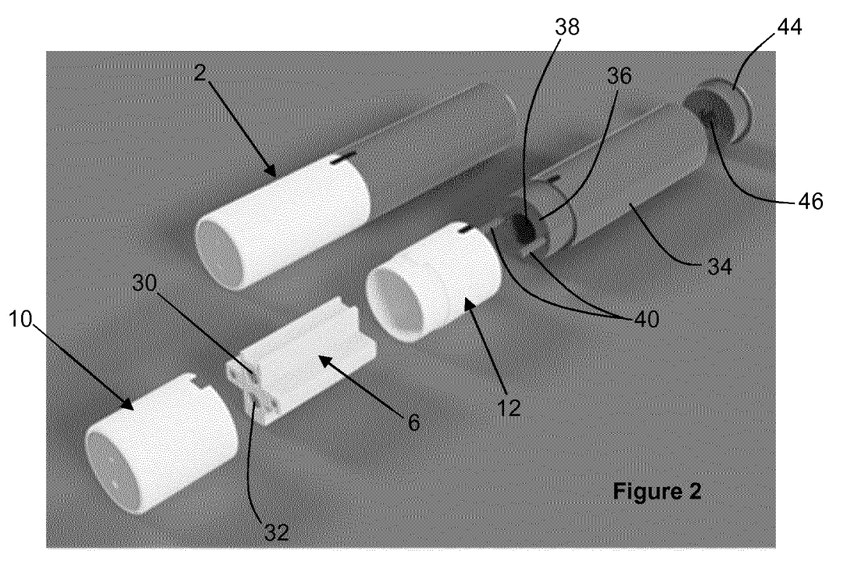
FIG. 2 shows an exploded view of the cartridge assembly of FIG. 1.

FIG. 1 shows a cartridge assembly 2 in accordance with an embodiment of the present invention and FIG. 2 shows an exploded view of the cartridge assembly 2. The cartridge assembly 2 comprises a housing 4, a cartridge 6 positioned in the housing 4, and a mouthpiece 8 positioned at a downstream end of the housing 4.

The housing 4 comprises an upstream housing part 10 and a downstream housing part 12, the upstream and downstream housing parts 10, 12 secured together by an interference fit to form the housing 4 with the cartridge 6 positioned therein.

The upstream housing part 10 comprises an upstream housing end wall 14, a third air inlet 16 provided in the upstream housing end wall 14, and a fourth air inlet 18 provided in the upstream housing end wall 14.

Figure 3:
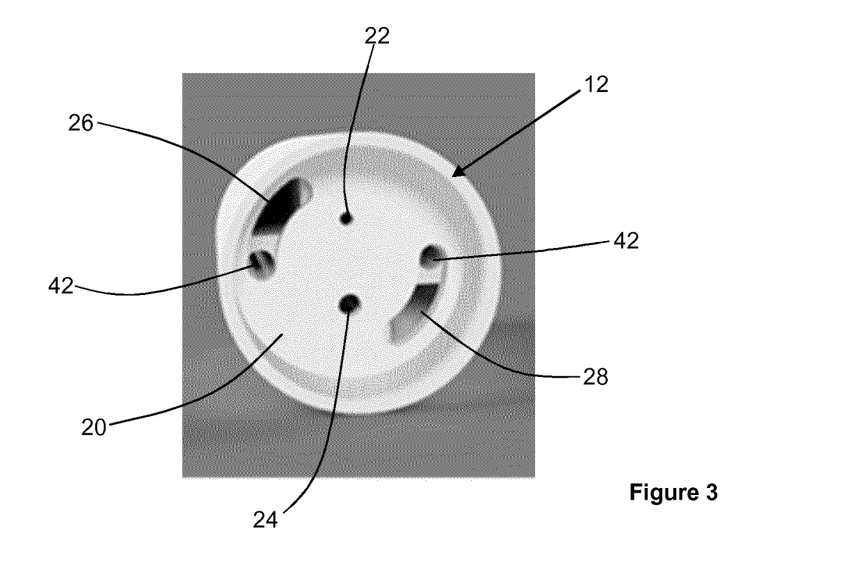
FIG. 3 shows a view of the downstream end of the housing of the cartridge assembly of FIG. 1.

As shown in FIG. 3, which shows the downstream end of the downstream housing part 12 and the cartridge 6 received therein, the downstream housing part 12 comprises a downstream housing end wall 20, a third air outlet 22 provided in the downstream housing end wall 20, and a fourth air outlet 24 provided in the downstream housing end wall 20. Also provided in the downstream housing end wall 20 are a first guide slot 26 and a second guide slot 28. The first and second guide slots are arcuate, each having a centre of curvature centred on the circular downstream housing end wall 20.

The cartridge 6 has a cross-shaped cross-sectional shape and comprises a first compartment 30 housing a nicotine source and a second compartment 32 housing an acid source. A susceptor is positioned between the first and second compartments 30, 32 for heating the first and second compartments 30, 32 via inductive heating of the susceptor using an inductive heater of an aerosol-generating device.

The mouthpiece 8 comprises a mouthpiece body 34 comprising an upstream mouthpiece end wall 36 in which a mouthpiece air inlet 38 is provided. A pair of linkages 40 in the form of elongate rods extend upstream from the upstream mouthpiece end wall 36. Each of the linkages 40 extends through one of the first guide slot 26 and the second guide slot 28 and engages a linkage aperture 42 provided in a downstream end of the cartridge 6. The upstream end of each linkage 40 is retained within the respective linkage aperture 42 by an interference fit.

A mouthpiece cap 44 is secured to a downstream end of the mouthpiece body 34 by an interference fit, the mouthpiece cap 44 defining a mouthpiece air outlet 46.

As a result of the first and second guide slots 26, 28 each having a centre of curvature centred on the circular downstream housing end wall 20, the mouthpiece 8 is rotatable with respect to the housing 4 by rotating the mouthpiece 8 so that the linkages 40 travel along the respective guide slots 26, 28. As a result of the linkages 40 being secured by an interference fit within the linkage apertures 42 on the cartridge 6, rotating the mouthpiece 8 with respect to the housing 4 also rotates the cartridge 6 with respect to the housing 4.

Figure 4:
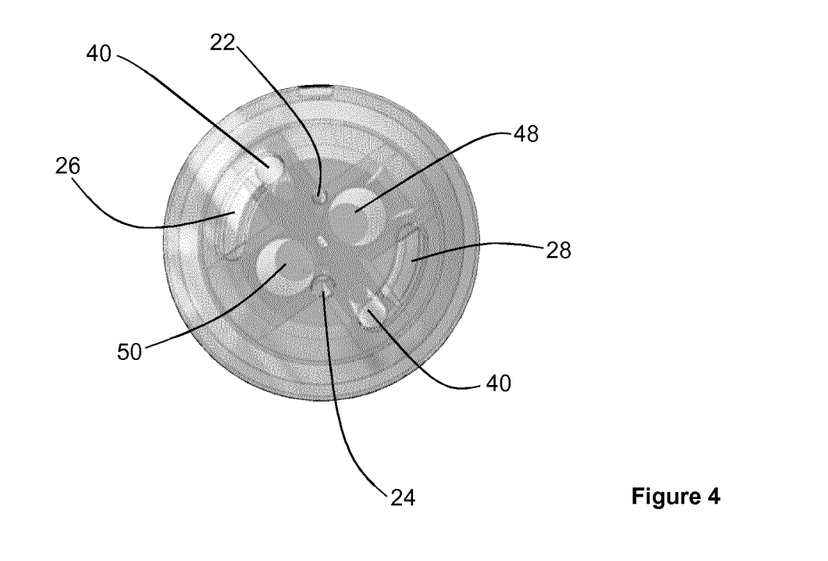
FIG. 4 shows a semi-transparent view of the downstream end of the housing of FIG. 3 with the cartridge in a first position.
Figure 5:
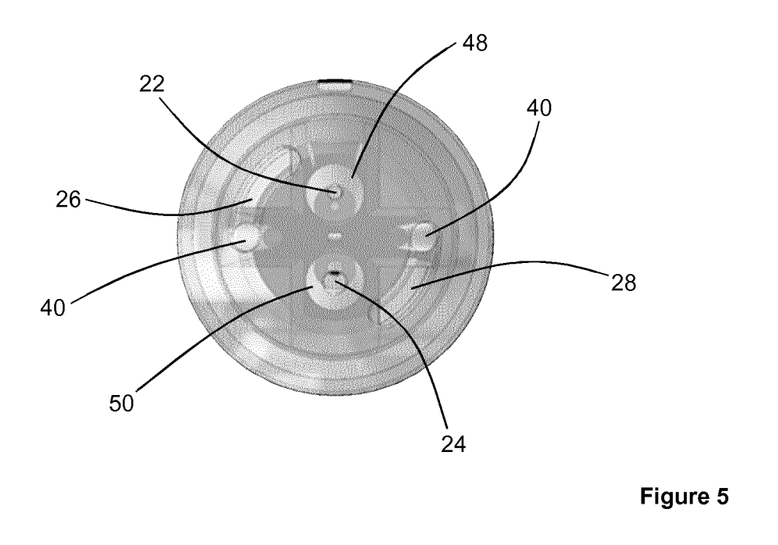
FIG. 5 shows a semi-transparent view of the downstream end of the housing of FIG. 3 with the cartridge in a second position.
Figure 6:
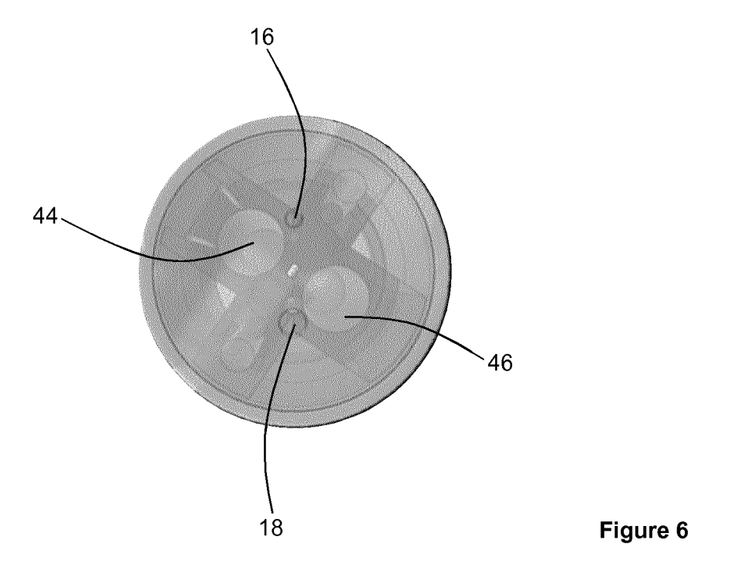
FIG. 6 shows a semi-transparent view of the upstream end of the housing of FIG. 3 with the cartridge in the first position.
Figure 7:
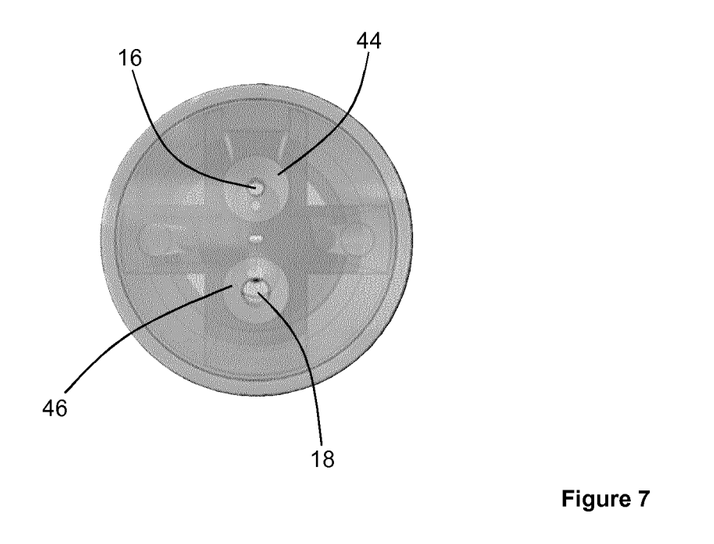
FIG. 7 shows a semi-transparent view of the upstream end of the housing of FIG. 3 with the cartridge in the second position.

FIGS. 4 and 5 show the downstream end of the housing 4, the housing 4 being depicted as semi-transparent so that the relative position of the cartridge 6 is visible. FIGS. 6 and 7 show the upstream end of the housing 4, the housing 4 being depicted as semi-transparent so that the relative position of the cartridge 6 is visible.

In use, the mouthpiece 8 and the cartridge 6 are rotatable with respect to the housing 4 between a first position shown in FIGS. 4 and 6 and a second position shown in FIGS. 5 and 7. In the first position, each linkage 40 is positioned within a first end of the respective guide slot 26, 28, as shown in FIG. 4. In the second position, each linkage 40 is positioned within a second end of the respective guide slot 26, 28, as shown in FIG. 5.

When the cartridge 6 is in the first position shown in FIGS. 4 and 6, the upstream housing end wall 14 obstructs a first air inlet 44 of the first compartment 30 and a second air inlet 46 of the second compartment 32, and the downstream housing end wall 20 obstructs a first air outlet 48 of the first compartment 30 and a second air outlet 50 of the second compartment 32. Therefore, when the cartridge 6 is in the first position, the loss of nicotine vapour and acid vapour from the first and second compartments 30, 32 respectively is substantially prevented.

When the cartridge 6 is rotated into the second position shown in FIGS. 5 and 7, the third air inlet 16 of the housing 4 is aligned with the first air inlet 44 of the cartridge 6, the fourth air inlet 18 of the housing 4 is aligned with the second air inlet 46 of the cartridge 6, the third air outlet 22 of the housing 4 is aligned with the first air outlet 48 of the cartridge 6, and the fourth air outlet 24 of the housing 4 is aligned with the second air outlet 50 of the cartridge 6. Therefore, when the cartridge assembly 2 has been activated by rotating the cartridge 6 into the second position, airflow paths are created through cartridge assembly 2 from the third and fourth air inlets 16, 18, through the first and second air inlets 44, 46, through the first and second compartments 30, 32, through the first and second air outlets 48, 50, through the third and fourth air outlets 22, 24, through the mouthpiece air inlet 38 and through the mouthpiece air outlet 46.

In use, when the cartridge assembly 2 has been activated, nicotine vapour is drawn into the mouthpiece 8 from the first compartment 30 and acid vapour is drawn into the mouthpiece 8 from the second compartment 32. The nicotine vapour and the acid vapour react in the gas phase in the mouthpiece 8 to create an aerosol of nicotine salt particles for delivery to the user through the mouthpiece air outlet 46.

The cartridge 6 and the mouthpiece 8 may be rotated back into the first position so that the housing 4 re-obstructs the first air inlet 44, the second air inlet 46, the first air outlet 48 and the second air outlet 50. This may substantially prevent the loss of remaining nicotine vapour and acid vapour from the first and second compartments 30, 32 respectively. The cartridge 6 and the mouthpiece 8 may be moveable repeatedly between the first and second positions to facilitate multiple uses of the cartridge assembly 2 and to substantially prevent the loss of nicotine vapour and acid vapour from the cartridge 6 when the cartridge assembly 2 is not being used.

The invention claimed is:

1. A cartridge assembly for an aerosol-generating system, the cartridge assembly comprising:
    a cartridge comprising:
        a first compartment having a first air inlet and a first air outlet, and
        a second compartment having a second air inlet and a second air outlet, a housing enclosing the cartridge, the housing comprising:
            an upstream housing end wall comprising a third air inlet and a fourth air inlet, and
            a downstream housing end wall comprising a third air outlet, a fourth air outlet, and at least one guide slot;
    a mouthpiece comprising an upstream mouthpiece end wall and a mouthpiece air inlet in the upstream mouthpiece end wall, the mouthpiece air inlet in fluid communication with the third air outlet and the fourth air outlet; and
    at least one linkage extending through the at least one guide slot and connected to the cartridge and the upstream mouthpiece end wall,
    wherein the mouthpiece and the cartridge are rotatable with respect to the housing from a first position to a second position,
    wherein, when the cartridge is in the first position, the upstream housing end wall obstructs the first air inlet and the second air inlet, and the downstream housing end wall obstructs the first air outlet and the second air outlet, and
    wherein, when the cartridge is in the second position, the third air inlet is in fluid communication with the first air inlet, the third air outlet is in fluid communication with the first air outlet, the fourth air inlet is in fluid communication with the second air inlet, and the fourth air outlet is in fluid communication with the second air outlet.

2. The cartridge assembly according to claim 1,
    wherein the at least one guide slot comprises a first guide slot and a second guide slot, and
    wherein the at least one linkage comprises a first linkage extending through the first guide slot and connected to the cartridge and the upstream mouthpiece end wall, and a second linkage extending through the second guide slot and connected to the cartridge and the upstream mouthpiece end wall.

3. The cartridge assembly according to claim 1,
    wherein the downstream housing end wall is substantially circular, and
    wherein the at least one guide slot has an arcuate shape.

4. The cartridge assembly according to claim 1,
    wherein the at least one guide slot comprises a first end and a second end,
    wherein, when the cartridge is in the first position, the at least one linkage is positioned at the first end of the at least one guide slot, and
    wherein, when the cartridge is in the second position, the at least one linkage is positioned at the second end of the at least one guide slot.

5. The cartridge assembly according to claim 1, wherein the angular rotation of the cartridge from the first position to the second position is between 30 degrees and 110 degrees with respect to the housing.

6. The cartridge assembly according to claim 1, wherein the cartridge and the mouthpiece are configured for two-way rotational movement with respect to the housing so that the cartridge is rotatable from the second position to the first position.

7. The cartridge assembly according to claim 1, wherein the at least one linkage comprises a rod extending between the upstream mouthpiece end wall and the cartridge.

8. The cartridge assembly according to claim 1, wherein the at least one linkage is formed integrally with the upstream mouthpiece end wall or with the cartridge.

9. The cartridge assembly according to claim 1,
    wherein the mouthpiece comprises a mouthpiece chamber positioned downstream of the upstream mouthpiece end wall and in fluid communication with the mouthpiece air inlet, and
    wherein the mouthpiece further comprises a mouthpiece air outlet at a downstream end of the mouthpiece chamber.

10. The cartridge assembly according to claim 9,
wherein the mouthpiece further comprises a ventilation air inlet providing fluid communication between the exterior of the mouthpiece and the mouthpiece chamber, and
wherein the ventilation air inlet is position between the upstream mouthpiece end wall and the downstream end of the mouthpiece chamber.

11. The cartridge assembly according to claim 1, wherein the cartridge further comprises a nicotine source positioned within the first compartment and an acid source positioned within the second compartment.

12. The cartridge assembly according to claim 1,
wherein the cartridge further comprises a third compartment configured to receive a heating element of an aerosol-generating device, the third compartment positioned between the first compartment and the second compartment, and
wherein the upstream housing end wall comprises an aperture aligned with the third compartment when the cartridge is in the second position.

13. The cartridge assembly according to claim 1, wherein the cartridge comprises a susceptor positioned between the first compartment and the second compartment.

14. An aerosol-generating system, comprising:
a cartridge assembly according to claim 1; and
an aerosol-generating device comprising a device cavity configured to receive an upstream end of the cartridge assembly and a heater configured to heat the first compartment and the second compartment of the cartridge of the cartridge assembly.

15. The aerosol-generating system according to claim 14,
wherein the heater comprises a heating element positioned within the device cavity,
wherein the cartridge comprises a third compartment configured to heat the heating element and positioned between the first compartment and the second compartment, and
wherein the housing comprises an aperture aligned with the third compartment when the cartridge is in the second position.

16. The aerosol-generating system according to claim 14,
wherein the heater comprises an inductive heater surrounding at least a portion of the device cavity, and
wherein the cartridge comprises a susceptor positioned between the first compartment and the second compartment.

* * * * *